United States Patent [19]

Rieman

[11] 4,289,132
[45] Sep. 15, 1981

[54] SURGICAL INSTRUMENT AND METHOD OF USING THE SAME

[76] Inventor: Robert D. Rieman, 2641 NE. 27th Ter., Fort Lauderdale, Fla. 33306

[21] Appl. No.: 51,746

[22] Filed: Jun. 25, 1979

[51] Int. Cl.³ ............................................. A61B 17/36
[52] U.S. Cl. ........................... 128/303.14; 128/303.17; 128/305
[58] Field of Search .......... 128/303 R, 303.14, 303.17, 128/303.13, 304, 305, 314, 751, 339, 329 R; 30/164.5, 366, 340, 343; 7/158, 160, 162

[56] References Cited

U.S. PATENT DOCUMENTS

| | | | |
|---|---|---|---|
| 818,152 | 4/1906 | Edwards | 128/339 |
| 1,639,996 | 8/1927 | Groff | 128/303.14 |
| 3,221,744 | 12/1965 | Stryker | 128/305 |
| 3,508,553 | 4/1970 | Kanbar et al. | 178/303 R |
| 3,741,214 | 6/1973 | Tillander | 128/303 R |
| 3,835,859 | 9/1974 | Roberts et al. | 128/305 |
| 3,877,570 | 4/1975 | Barry | 128/339 X |
| 3,920,023 | 11/1975 | Dye et al. | 128/347 |
| 4,067,340 | 1/1978 | Le Noir | 128/305 |

FOREIGN PATENT DOCUMENTS 10620 of 1888 United Kingdom .................. 30/343

Primary Examiner—Stephen C. Pellegrino
Assistant Examiner—Michael H. Thaler
Attorney, Agent, or Firm—O'Brien and Marks

[57] ABSTRACT

A surgical instrument has a slender rod with a sharp point which is pushed inside out through skin tissue at a location remote from an incision so that the rod can be manipulated to perform a surgical procedure at the remote location by means of a surgical tool mounted on the other end of the rod.

An electro-meniscectome has a handle supporting an insulative blade holder which insulates a portion of a cutting blade and which has a pair of guides extending forward from opposite sides of the blade. The cutting blade is connected to an energizing wire.

10 Claims, 15 Drawing Figures

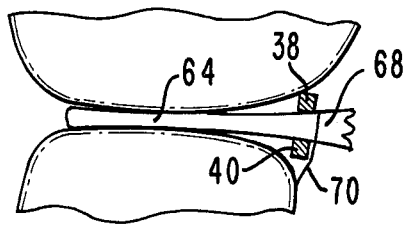
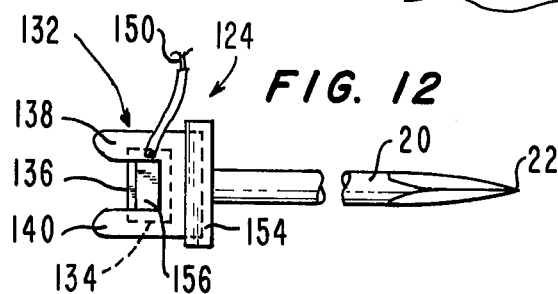
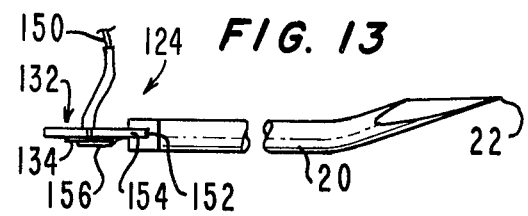
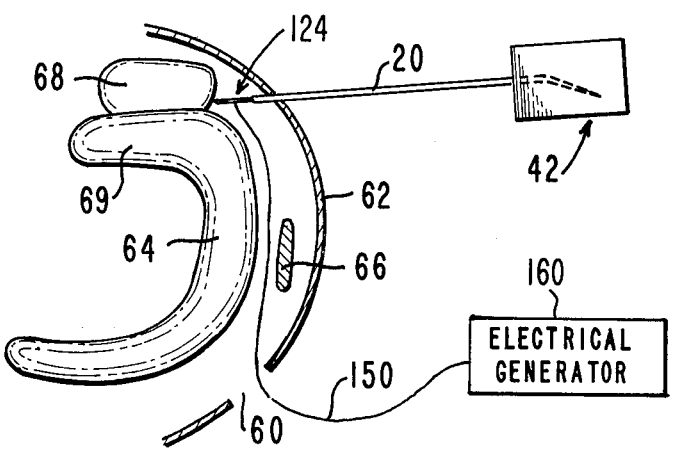
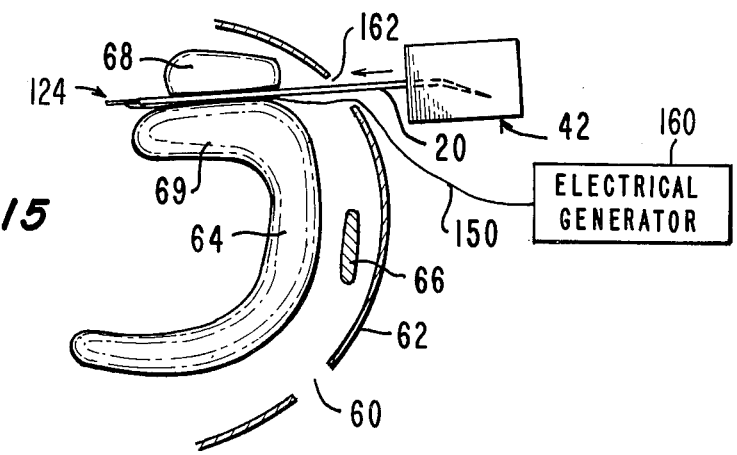

SURGICAL INSTRUMENT AND METHOD OF USING THE SAME

TECHNICAL FIELD

The present invention relates to surgical instruments, as well as methods of using such surgical instruments, for performing surgical procedures at locations remote from an incision, such as cutting the posterior attachments of a meniscus or cartilage in a knee.

DESCRIPTION OF THE PRIOR ART

In surgically removing a damaged meniscus (either medial or lateral) of a knee, an anterior or frontal incision is commonly employed for access to the meniscus. The anterior portion of the meniscus is usually detached first, and then the other peripheral attachments are severed proceeding along the meniscus inside the collateral ligament to the posterior attachments. After the posterior attachments are severed, the meniscus is displaced into the intercondylar notch so that the attachment to the bone at the posterior horn can be viewed and divided to free the meniscus for removal.

The anterior and central attachments of the meniscus are visible and accessible for being severed by conventional procedures utilizing conventional surgical instruments. However the posterior peripheral attachments of the meniscus, particularly to the synovial tissue, are not visible through the anterior incision and are relatively inaccessible. One type of prior art instrument or cartilage knife for separating the posterior attachments has a handle with a curved shaft supporting a blade at one end with a forward transverse cutting edge and with guide members extending forward on opposite sides of the cutting blade. This cutting blade is inserted through the anterior incision and through the opening inside of the collateral ligament, and is then manipulated around an almost right angle corner to cut the posterior attachments. This cutting is not visible through the anterior incision and it is difficult to manipulate the conventional instruments around the corner, in spite of the curved forward end of the instrument, to perform the posterior detachment. Often a portion of the posterior synovial attachment is left unsevered so that when displacement of the meniscus into the intercondylar notch is attempted, the posterior synovial attachments are stretched and placed under tension. Additional attempts must be then made to sever these posterior attachments without leaving a large part of the posterior portion of the meniscus behind. Typically, the meniscus, after being completely removed, has large clumps of the posterior synovial tissue attached thereto, indicating the difficulty in performing these posterior detachments. This trauma to the posterior synovium is a major factor in causing post-operative pain and slow rehabilitation of a patient.

In one alternative prior art procedure, a second incision is made behind the collateral ligament, and the posterior detachment of the meniscus is performed by inserting the cartilage knife through this second incision against the posterior synovial attachments to detach the posterior portion of the meniscus. However this alternate procedure involves a second incision increasing the post-operative pain and rehabilitation time as well as increasing the chance of complications.

The prior art, as exemplified in U.S. Pat. No. 3,835,859 and No. 4,067,340, contains a number of surgical instruments designed to perform the posterior detachments of the meniscus. These prior art surgical instruments are relatively difficult to use and sometimes fail to provide the desired detachment of the posterior portion of the meniscus.

Hemostasis, or the stopping of active bleeding, is very difficult to achieve in an meniscectomy because of the inaccessibility of the posterior portion of the knee joint. Thus a meniscectomy is almost always performed with a tourniquet on the upper thigh, and the tourniquet is not released until the surgical operation has been completed and a dressing and compressive bandage applied to the knee joint which usually fills with blood. This post-operative bleeding contributes to the patient's pain and discomfort and the slowing of post-operative recovery.

SUMMARY OF THE INVENTION

The invention, in a first aspect, is summarized in a surgical instrument including a slender rod having a sharp point at one end for being inserted inward through an incision and then outward by penetration through skin tissue at a location remote from the incision, and a tool mounted on the other end of the rod for being manipulated by a portion of the rod extending outside of the skin tissue to perform a surgical procedure.

The invention, in a second aspect, is summarized in an electrical surgical instrument for coagulation and for cutting at least a posterior attachment of a meniscus in a knee, including a handle, an electrically insulative blade holder mounted on the handle, a metal blade having a forward transverse cutting edge mounted in the blade holder, an insulation-covered electrical wire connected to the blade for connecting the blade to a surgical electrical generator, the blade-holder including a pair of guide members extending forward on opposite sides of the blade for guiding the blade against the at least posterior knee meniscus attachment, and the metal blade being insulatively covered by means including the blade holder so that only the the forward cutting portion of the blade is exposed.

An object of the invention in accordance with the first aspect is to provide a surgical instrument, as well as a procedure for using the same, which renders the performance of surgical procedures at positions remote and relatively inaccessible from an incision much easier.

Another object of the invention is to reduce the post-operative discomfort and rehabilitation time of a patient.

One advantage of the invention is that difficult procedures, such as the posterior detachment of a meniscus, can be performed much more exactly and quickly with substantially less trauma than has been previously attainable.

A feature in accordance with the second aspect of the invention is that substantial hemostasis in a meniscectomy is made possible.

Other objects, advantages and features of the invention will be apparent from the following description of the preferred embodiment taken in conjunction with the accompanying drawings.

BRIEF DESCRIPTION OF THE DRAWINGS

FIG. 11 is a cross-sectional side view of a knee portion illustrating the step of FIG. 10.

FIG. 12 is a plan view of a modified surgical instrument, with a portion broken away, in accordance with the invention.

FIG. 13 is a side view of the instrument of FIG. 12.

FIG. 14 is a cross-sectional view of a knee illustrating the employment of the modified surgical instrument of FIGS. 12 and 13.

FIG. 15 is a cross-sectional view of a knee portion illustrating a modified procedure for the employment of the surgical instrument of FIGS. 12 and 13.

DESCRIPTION OF THE PREFERRED EMBODIMENT

Figure 1:
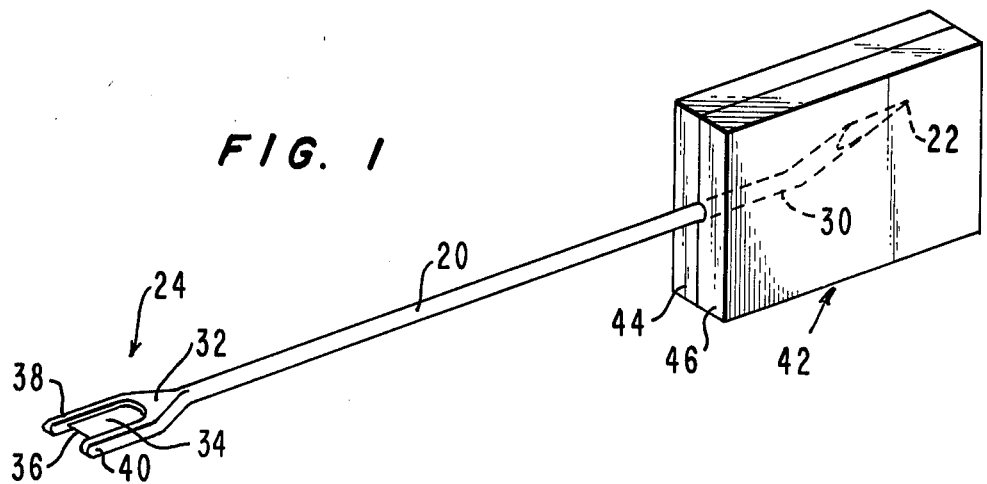
FIG. 1 is a perspective view of a surgical instrument for use in a meniscectomy in accordance with the invention.
Figure 2:
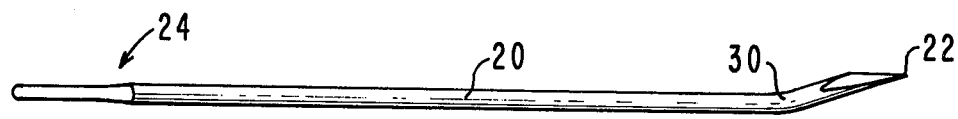
FIG. 2 is a side view of a blade and rod portion of the instrument of FIG. 1.
Figure 3:
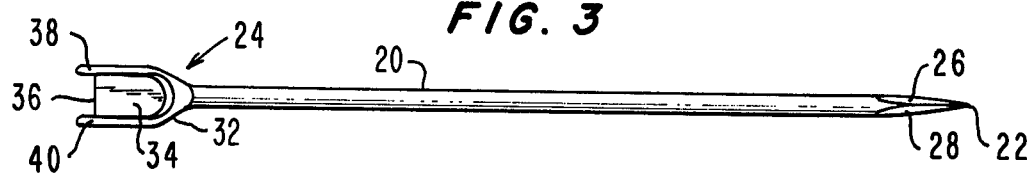
FIG. 3 is a plan view of the blade and rod portion of FIG. 2.
Figure 4:
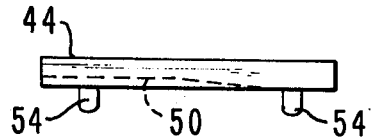
FIG. 4 is a side view of one half of a handle and point guard portion of the instrument of FIG. 1.
Figure 5:
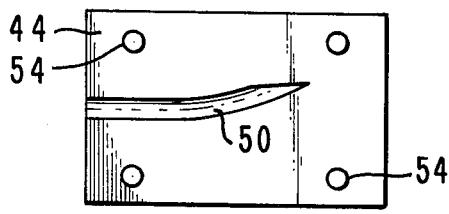
FIG. 5 is a plan view of the half handle portion of FIG. 4.
Figure 6:
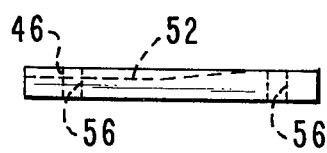
FIG. 6 is a side view of the other half of the handle and point guard portion of the instrument of FIG. 1.
Figure 7:
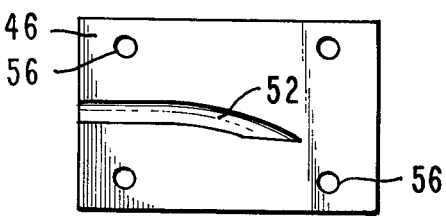
FIG. 7 is a plan view of the half handle portion of FIG. 6.

As shown in FIG. 1, a surgical instrument for performing a surgical procedure at a position relatively remote and inaccessible from an incision, such as detachment of a posterior portion of a meniscus, includes a slender rigid rod 20 which has a sharp point 22 formed at one end and a tool indicated generally at 24, mounted on the opposite end. The rod 20 is illustrated in FIGS. 1-3 as having a round cross-section and the point 22 is shown as being formed by grinding two flat surfaces 26 and 28 to form a generally three-sided point similar to the points employed in a trocar; however, any type of slender rigid rod and any sharp point can be used. Preferrably a portion 30 of the rod 20 adjacent the point 22 is curved or bent to form an obtuse angle with the remaining portion of the rod which is straight. The tool 24 is shown as being a conventional configuration utilized in detaching a meniscus. Such tool 24 includes a blade holder portion 32 which supports or has a cutting blade 34 having a forward cutting edge 36 extending transverse or perpendicular to the rod 20. The tool holder 32 has guides 38 and 40 which extend forward parallel to the rod 20 past the cutting edge 36 on opposite lateral edges of the cutting blade 34. The guides 38 and 40 are spaced so as to extend above and below a peripheral portion of the meniscus in order to guide the tool in performing the detachment of the meniscus from the synovial tissue.

In a prototype of the instrument of FIGS. 2 and 3, a rod with a pointed end from a trocar is welded onto a conventional cartilage cutting tool to form the instrument.

A protective guard and handle indicated generally at 42 may be placed over the sharp point 22 of the instrument to protect the surgeon from injury from the sharp point and to enable easier manipulation of the instrument. One suitable guard and handle 42 includes a pair of members or portions 44 and 46 which as illustrated in FIGS. 4-7 have mating grooves 50 and 52, respectively, for receiving the pointed end 22 and curved portion 30 of the rod 20. Projections 54 are formed on the member 44 for snapping into suitably formed openings 56 in the member 46 to releasably hold the members together. These handle members 44 and 46 can be formed from a plastic or any other material suitable for being sterilized and used in a surgical procedure. Alternatively, single piece or other multipiece protective guards and handles may be utilized, or various other conventional techniques may be used to hold multiple handle parts together; for example, a clamp can be employed to hold two handle members together in place of interlocking portions of the member. It is preferred that the handle portion 42 interlock with the curved portion 30 and the point 22 of the rod 20 so that the handle 42 can be used to turn the rod 20 and tool 24 about an axis through the rod 20.

Figure 8:
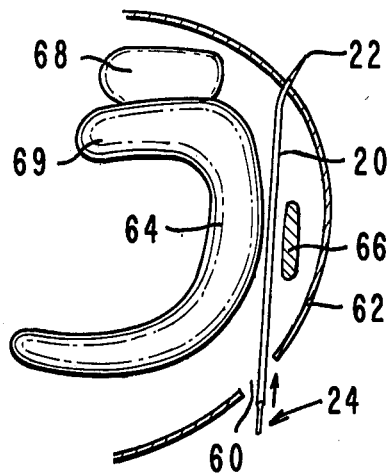
FIG. 8 is a cross-section view of a portion of a knee illustrating one step in the procedure for using the instrument of FIG. 1.
Figure 9:
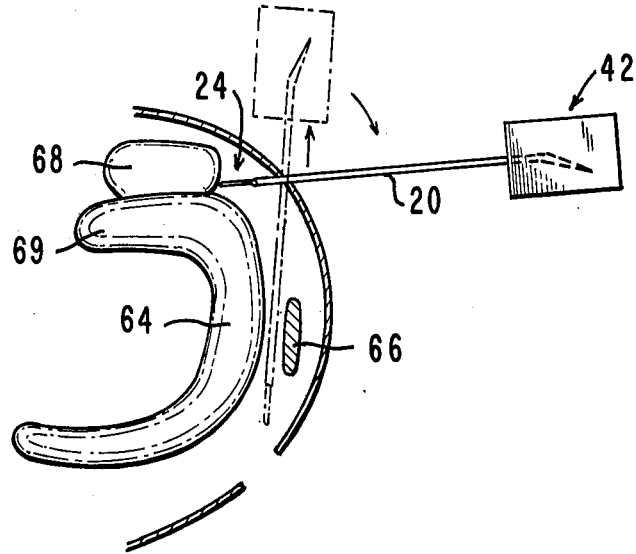
FIG. 9 is a view similar to FIG. 8 but illustrating subsequent steps in the use of the surgical instrument of FIG. 1.

The method of using the surgical instrument of FIG. 1 is illustrated in FIGS. 8-11. Previously an anterior incision 60 will have been made through the skin and other tissues 62 covering the anterior portion of the joint, and preferably, the anterior and central portions of the meniscus 64 will have been detached using the present instrument or any other instrument in a conventional manner. With the handle 42 removed, the pointed end 22 of the slender rod 20 is passed through the incision 60 and the opening between the meniscus 64 and the collateral ligament 66 to a position to the rear or behind the ligament 66 adjacent to the posterior portion of the meniscus. At this point, the sharp point 22 is forced through the skin tissues 62. Then, as shown in FIG. 9, the protective guard and handle 42 is placed on the sharp point 22 and the rod 20 is pulled to pull the tool 24 to the rear of the ligament 66 whereupon the rod 20 is pivoted about the point where it passes through the outer tissue 64 so as to be generally aligned with the attachment of the posterior portion 69 of the meniscus 64 with the synovial tissue 68. The alignment of this tool 24 may be viewed through the incision 60 to insure that the tool 24 is approximately positioned to engage the guides 38 and 40 below and above the peripheral portion of the meniscus 64 as shown in FIG. 11. Then the handle 42 and rod 20 are pushed generally in a straight line to detach the posterior portion of the meniscus 64 from the synovial tissue 68. Also the detachment detaches the coronary ligament 70, FIG. 11, from the posterior portion of the meniscus 64.

After completion of the cutting of the posterior peripheral meniscus attachments, the removal of the meniscus is completed in a conventional manner. This involves the displacement of the meniscus into the intercondylar notch and the severing of the attachment of the posterior horn to the bone.

Figure 10:
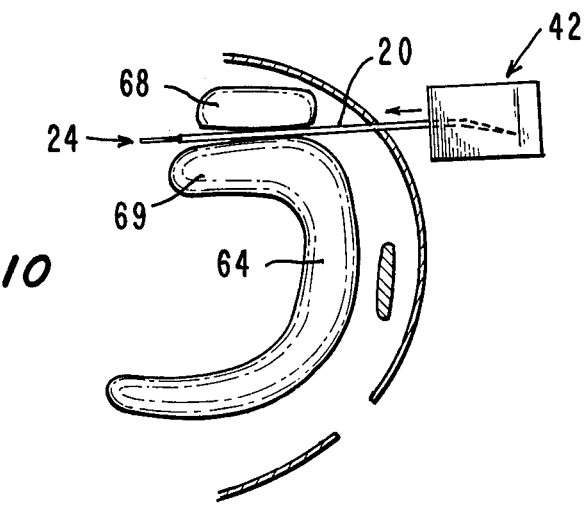
FIG. 10 is a view similar to FIGS. 8 and 9 but illustrating a still further step in the use of the instrument of FIG. 1.

The surgical instrument is removed by reversing the steps illustrated in FIGS. 8-10. The handle 42 and rod 20 are pulled back and pivoted so that the tool 24 can be pushed back through the space between the meniscus 64 and the ligament 66 to protrude out of the incision 60. The guard 42 is then removed and the tool end 24 of the instrument gripped and pulled to remove the instrument.

The present instrument and procedure for using the instrument render the detachment of the posterior portion of the meniscus from the synovium and coronary ligament substantially easier with substantially reduced trauma to the synovial tissue and substantially less chance of leaving large portions of the meniscus still attached. Employing a pushing action directly on the present surgical instrument while it is aligned generally along the line of detachment is substantially easier than trying to manipulate a curved instrument around a right angle corner. Since the synovial tissue is subjected to substantially less trauma, the post-operative pain and bleeding is substantially reduced. Further the penetration of the instrument through the skin tissue behind the collateral ligament is only a puncture and does not involve an incision; thus complications and procedures of posterior incisions are avoided.

A modified surgical instrument, particularly for electro-surgical procedures, is shown in FIGS. 12 and 13. A tool indicated generally at 124 includes an insulative blade holder indicated generally at 132 and a metal blade 134 secured to the insulative holder 132. The holder 132 is mounted on the rod 20 and has guides 138 and 140 formed thereon similar in configuration to the guides 38 and 40 of the tool of FIGS. 1–3. An electrical wire 150 with an insulative coating is electrically connected to the metal blade 134 by soldering, welding or other electrical connection. The connected end of the wire 150 as well as the metal blade 134 is insulated by the insulative holder 132 as well as an insulative coating 156 except for the cutting edge 136 of the blade 134 which is left exposed.

In a prototype version of the electro-surgical instrument, the blade holder 138 is formed from a high-dielectric high-temperature plastic material type G10 normally used in printed circuit boards. The wire 150 passes through an opening in the holder 138 and is soldered to the blade 134 which is bonded by an epoxy adhesive to one side of the holder 132. The epoxy material is also used to form the insulative coating 156. The holder 132 is secured within a slot 152 in a bar 154 welded on the tool end of the rod 20. Any other type of insulative blade holder, such as a metal holder suitably coated with an insulative material, and other arrangements for mounting the blade 134 or forming the blade integral with the holder and for insulating the blade and holder can be used.

The electro-surgical instrument of FIGS. 12 and 13 can be used to make all of the detachments of the meniscus including the anterior, central, posterior and bone detachments; the blade 134 being energized during each detachment to produce simultaneous electro-cutting and electro-coagulation. In one method of making a posterior detachment, the instrument is positioned in a manner substantially similar to the positioning of the tool of FIGS. 1–3, except that the wire 150 passes from the cutting blade of the tool 124 inside the ligament 66 and out the incision 60 as shown in FIG. 14. This wire 150 is connected to a conventional electrical surgical generator 160 which generates a suitable high frequency electrical voltage for aiding in the cutting and for performing electro-coagulation or cauterization during the cutting. Thus when the rod 20 and handle 42 are pushed, the tool 124 performs the posterior peripheral detachment of the meniscus 64 and simultaneously performs electrocoagulation. Removal of the meniscus 64 and the surgical instrument proceed in a manner similar to that employed with the tool of FIGS. 1–3.

A modified procedure for employing the electro-surgical instrument of FIGS. 12 and 13 in performing a posterior detachment is illustrated in FIG. 15. In this modified procedure a second incision 162 is formed through the skin and outer tissues 62 behind the ligament 66. The tool 124 with the attached wire 150 are inserted through the second incision 162 and the posterior detachment is performed with the electrical include a plastic handle or other type of handle in place of the pointed rod 20 since the pointed end is not needed with the separate incision 162 being made.

The tool 124 by performing both electro-cutting and electro-coagulation results in hemostasis which allows the surgeon to release the tourniquet after the meniscus has been removed. Thus post-operative bleeding is eliminated speeding the recovery of the patient and reducing post-operative pain.

It is noted that the insulative blade holder 132 performs a dual function, i.e., the blade holder insulates at least a portion of the blade 134 and also has the guides 138 and 140 for guiding the tool on the upper and lower sides of the peripheral portions of the meniscus where it is attached. This electro-surgical tool provides for a substantially improved operating procedure for detaching the meniscus and for producing hemostasis which has previously been generally unattainable in meniscectomies.

Since the present invention is subject to many variations, modifications and changes in detail, it is intended that the foregoing description and the accompanying drawings be interpreted as illustrative and not in a limiting sense.

What is claimed is:

1. A surgical instrument comprising
   a slender rigid rod having a sharp point at one end for being inserted inward through an incision and then outward by penetration through skin tissue at a location remote from the incision;
   a tool mounted on the other end of the rod for being manipulated by a portion of the rod extending outside of the skin tissue to perform a surgical procedure; and
   said tool including an insulative blade holder, a metal blade mounted in the blade holder, and an insulation coated electrical wire connected to the blade for connecting the blade to an electrical surgical generator.

2. A method of performing a surgical procedure at a position relatively remote and inaccessible from an incision, comprising the steps of
   inserting a sharp pointed end of a slender rigid rod through the incision,
   pushing the sharp pointed end through the skin tissue from the inside outward at a point adjacent the remote and inaccessible position,
   manipulating a portion of the rod extending outside the skin tissue to perform a surgical procedure at the remote and inaccessible position by means of a tool mounted on the other end of the rod, and
   applying an electrical signal to the tool to perform coagulation and cutting.

3. A method as claimed in claim 2 including the step of attaching a protective handle on the sharp pointed end after the pushing step and prior to the manipulating step.

4. A method of detaching a posterior portion of a meniscus in a knee, comprising the steps of inserting a sharp pointed end of a slender rigid rod through an anterior incision and through an opening between the meniscus and a collateral ligament, pushing the sharp pointed end through skin tissue from the inside out to the rear of the collateral ligament at a position adjacent the posterior attachment of the meniscus, and manipulating a portion of the rod extending outside of the skin tissue including pushing the rod to perform a surgical detachment of the posterior portion of the meniscus by means of a cartilage cutting tool mounted on the other end of the rod.

5. A method as claimed in claim 4 including the step of attaching a removable handle on the sharp pointed end of the rod after the pushing step but prior to the manipulating step.

6. A method as claimed in claim 4 or 5 including the step of applying an electrical signal to an exposed cutting edge of a metal blade which has its remaining portion insulated during the manipulating step so as to simultaneously perform electro-coagulation with the detaching.

7. A surgical instrument for detaching a posterior portion of a meniscus in a knee comprising a slender rigid rod having a sharp point at one end for being inserted through an anterior incision, inside a collateral ligament and then outward by penetration through skin tissue at a location behind the collateral ligament; and a cartilage cutting tool mounted on the other end of the rod for being manipulated by a portion of the rod extending outside of the skin tissue to perform a surgical procedure, said tool including an electrically insulative blade holder mounted on the handle, a metal blade having a forward transverse cutting edge mounted in the blade holder, an insulation coated electrical wire connected to the blade for connecting the blade to a surgical electrical generator, said blade holder including a pair of guide members extending forward on opposite sides of the blade for guiding the blade against a posterion knee meniscus attachment, and said metal blade being insulatively covered by means including said blade holder so that only the forward cutting edge of the blade is exposed.

8. A surgical instrument as claimed in claim 7 wherein the blade holder is formed entirely from an electrically insulative material.

9. A surgical instrument as claimed in claim 8 wherein the electrical wire passes through an opening through the blade holder.

10. A surgical instrument for detaching a posterior portion of a meniscus in a knee comprising a slender rigid rod having a sharp point at one end for being inserted through an anterior incision, inside a collateral ligament and then outward by penetration through skin tissue at a location behind the collateral ligament;

a cartilage cutting tool mounted on the other end of the rod for being manipulated by a portion of the rod extending outside of the skin tissue to perform a surgical procedure; and said cartilage cutting tool including an insulative blade holder, a metal blade mounted in the blade holder, and an insulation coated electrical wire connected to the blade for connecting the blade to an electrical surgical generator.

* * * * *